(12) United States Patent
Dummer

(10) Patent No.: US 6,928,891 B2
(45) Date of Patent: Aug. 16, 2005

(54) MATERIAL SAMPLE PREPARATION APPARATUS AND METHOD

(75) Inventor: Andrew K. Dummer, Durham, NC (US)

(73) Assignee: Troxler Electronic Laboratories, Inc., Research Triangle Park, NC (US)

(*) Notice: Subject to any disclaimer, the term of this patent is extended or adjusted under 35 U.S.C. 154(b) by 0 days.

(21) Appl. No.: 10/409,345

(22) Filed: Apr. 8, 2003

(65) Prior Publication Data

US 2004/0200296 A1 Oct. 14, 2004

(51) Int. Cl.[7] .............................. G01N 1/38; G01N 1/44
(52) U.S. Cl. .............................. 73/863.01; 73/863.11; 366/4; 366/7; 366/60
(58) Field of Search .............................. 73/863–863.01, 73/863.11, 866; 436/55, 174; 366/4, 7, 22, 24, 25, 54, 60

(56) References Cited

U.S. PATENT DOCUMENTS

| | | | | |
|---|---|---|---|---|
| 3,554,038 A | * | 1/1971 | Powell et al. ............ | 73/863.83 |
| 3,631,712 A | * | 1/1972 | Mercier ..................... | 73/54.03 |
| 4,097,925 A | * | 6/1978 | Butler, Jr. .................. | 366/2 |
| 4,756,855 A | * | 7/1988 | Mathis et al. ........ | 73/863.01 X |
| 5,082,553 A | * | 1/1992 | Tanii ........................... | 209/3 |

OTHER PUBLICATIONS

"Standard Test Method for Theoretical Maximum Specific Gravity and Density of Bituminous Paving Mixtures," ASTM D2041–95, ASTM (USA), p. 176–182, (1995).

* cited by examiner

Primary Examiner—Thomas P. Noland
(74) Attorney, Agent, or Firm—Jenkins, Wilson & Taylor P.A.

(57) ABSTRACT

An automated apparatus for preparing material samples includes a rotatable drum support assembly, a drum rotatably contacting the drum support assembly, a fan, and a powered drive mechanism. The drum includes a hollow main section and first and second hollow end sections attached to the main section. The first hollow end section includes a first end wall tapering to a first outer aperture. The second hollow end section includes a second end wall tapering to a second outer aperture. The fan is mounted approximate to the first outer aperture for establishing forced air flow through the drum toward the second outer aperture. The drive mechanism rotatably communicates with the drum support assembly for rotating the drum. The apparatus is useful for preparing samples such as paving materials for test such as the determination of specific gravity and absorption.

11 Claims, 6 Drawing Sheets

MATERIAL SAMPLE PREPARATION APPARATUS AND METHOD

TECHNICAL FIELD

The present invention generally relates to material sample preparation. More particularly, the present invention relates to the preparation of samples of paving materials, including bituminous materials and aggregates, for subsequent measurement of properties such as specific gravity.

BACKGROUND ART

Samples of solid materials, and particularly road and paving materials such as bituminous mixtures and aggregates, are commonly subjected to standardized tests to determine certain properties such as specific gravity. For example, ASTM International has published the following standards, the contents of which are incorporated herein: ASTM D 2041—95, entitled "Standard Test Method for Theoretical Maximum Specific Gravity and Density of Bituminous Paving Mixtures" (also known and referred to hereinafter as "the Rice test"); and ASTM C 128—97, entitled "Standard Test Method for Specific Gravity and Absorption of Fine Aggregate" (hereinafter "the fine aggregate test"). Results from such tests are used both for the purpose of design and quality control.

The Rice test is employed to determine the theoretical maximum specific gravity and density of uncompacted bituminous paving mixtures at 25° C. Prior to subjecting the sample paving material to the Rice test, the sample must be prepared so as to be uncompacted, meaning that the sample must be brought to a loose, cool state. The conventional preparation method requires that a technician manually separate the particles of the sample so that the particles of the fine aggregate portion are no larger than 6.3 mm (¼ inch) each. This preparation process is labor intensive and time consuming, as it involves heating a sample to 100+/−° C. in an oven, and stirring the heated sample in a flat pan for twenty minutes or more while the pan is positioned in front of a fan.

The fine aggregate test is employed to determine bulk specific gravity (for example, the percentage of voids in a mineral aggregate) and absorption (for example, the amount of asphalt binder absorbed by the aggregate) on the basis of the weight of a sample aggregate that has reached a saturated-surface-dry (SSD) condition after being immersed in water for twenty-four hours. Thus, preparation of an aggregate sample for the fine aggregate test requires drying the sample to the SSD state. The conventional dry back method for fine aggregate, as described in ASTM C128-97, is performed manually or with the use of a mechanical tumbler, and the sample is frequently tested for SSD condition using one of three methods described therein. Typically, this process takes at least two hours and, accordingly, like the preparation required for the Rice test, is labor intensive and time consuming.

It would therefore be advantageous to provide an automated apparatus adapted to perform a sample preparation process, whether in preparation for the Rice test, the fine aggregate test, other tests, or for mixing. Such an automated apparatus would significantly reduce the expenditure of time and labor conventionally involved in material sample preparation, thereby allowing the technician to perform other tasks while the sample is being prepared by the apparatus. In addition, particularly in the case of fine aggregates, a need is recognized for developing more accurate and reproducible test methods. See, e.g., Kandhal et al., "Measuring Bulk-Specific Gravity of Fine Aggregates," Transportation Research Record 1721, Paper No. 00-1230, p. 81 (2000). The need for improved accuracy and reproducibility can be addressed by the use of an automated apparatus, since the automation would reduce the degree of subjectivity and manual effort involved in the sample preparation.

Kandhal et al. have proposed an automated technique for preparing a fine aggregate sample for the testing of bulk specific gravity. Their technique involves placing a wet sample of fine aggregate in a rotating drum and subjecting the sample to a steady flow of warm air. The temperature gradient of the incoming and outgoing air and the relative humidity of the outgoing air are monitored to establish the SSD condition. The drum was equipped with screens to confine the sample in the drum. However, it has been found that a drum such as that proposed by Kandhal et al. allows an unacceptable amount of sample to be lost through the inlet and outlet of the drum. This material loss is a consequence of the air flowing through the drum carrying away sample particles as the sample is being dried and/or cooled, as well as a result of the rotation of the drum and comcomitant agitation and movement of the sample. It would therefore also be advantageous to provide an automated apparatus adapted to perform a sample preparation process while preventing or at least reducing the amount of material loss unrelated to drying of the sample.

DISCLOSURE OF THE INVENTION

The present invention provides an automated apparatus and related method for the preparation of samples such as bituminous materials and fine aggregates, wherein the apparatus comprises a rotatable drum structured so as to prevent or at least reduce the amount of material loss from the drum.

According to one embodiment, an automated apparatus for preparing material samples comprises a rotatable drum support assembly, a drum rotatably contacting the drum support assembly, a fan, and a powered drive mechanism. The drum comprises a hollow main section having first and second open ends, and first and second hollow end sections attached to the main section. The first hollow end section comprises a first inner aperture communicating with the first open end, and a first outer aperture, and a first end wall tapering from the first inner aperture to the first outer aperture. The second hollow end section comprises a second inner aperture communicating with the second open end, a second outer aperture, and a second end wall tapering from the second inner aperture to the second outer aperture. The fan is mounted proximate to the first outer aperture, and establishes forced air flow through the drum towards the second outer aperture. The drive mechanism rotatably communicates with the drum support assembly for rotating the drum.

According to another embodiment, an automated apparatus for preparing material samples comprises first and second axles spaced in generally parallel relation, a drum rotatably supported by the first and second axles, a fan, and a motor. The drum comprises a hollow main section having first and second open ends, a hollow first frustoconical section, and a hollow second frustoconical section. The first frustoconical section is attached to the first open end and comprises a first outer aperture. The second frustoconical section is attached to the second open end and comprises a second outer aperture. The fan is mounted proximate to the first outer aperture. Upon activation, the fan establishes a forced air flow through the drum toward the second outer aperture. The motor communicates with the first axle to drive the rotation of the drum.

According to a method for preparing a material sample, the sample is placed in a drum comprising a hollow main section, a hollow first tapered section, and a hollow second tapered section. The main section has first and second open ends. The first tapered section is attached to the first open end and tapers to a first outer aperture. The second tapered section is attached to the second open end and tapers to a second outer aperture. The drum is rotatably supported on a support assembly. After the sample has been placed in the drum, the drum is rotated. A flow of air is conducted through the drum, whereby heat transfer occurs between the air and the sample. A property of the sample is monitored. When the property reaches a desired value, the motor is de-activated to cease rotation of the drum. The sample can then be removed from the drum and subjected to a desired test such as the determination of the specific gravity of the sample, the absorption of the sample, or any other suitable test.

In another method for preparing a material sample, a heated sample is placed in a drum structured according to embodiments disclosed herein and rotatably supported on a support assembly. A motor connected to the support assembly is activated to rotate the drum. The sample is cooled by activating a fan to establish forced air flow through the drum. A temperature of the sample is monitored. When the sample temperature reaches a desired sample temperature, the motor is de-activated to cease rotation of the drum. According to one aspect of this method, the sample temperature is monitored by monitoring a temperature of the drum.

In yet another method for preparing a material sample, a wet sample is placed in a drum structured according to embodiments disclosed herein and rotatably supported on a support assembly. A motor connected to the support assembly is activated to rotate the drum. The sample is dried by activating a fan to establish forced air flow through the drum. The sample is monitored to determine whether the sample has reached a saturated-surface-dry state. When it is determined that the sample has reached the saturated-surface-dry state, the motor is de-activated to cease rotation of the drum. According to one aspect of this method, the saturated-surface-dry state of the sample is determined by monitoring a mass of the sample, and the saturated-surface-dry state is defined when the rate of change in the sample mass has fallen below a prescribed level.

It is therefore an object of the present invention to provide an automated apparatus for preparing material samples that automates the sample preparation process.

It is another object of the present invention to provide a material sample preparation apparatus that includes a rotating drum in which a sample is tumbled and is capable of preventing substantial loss of material during rotation of the drum.

Some of the objects of the invention having been stated hereinabove, and which are addressed in whole or in part by the present invention, other objects will become evident as the description proceeds when taken in connection with the accompanying drawings as best described hereinbelow.

DETAILED DESCRIPTION OF THE INVENTION

Figure 1:
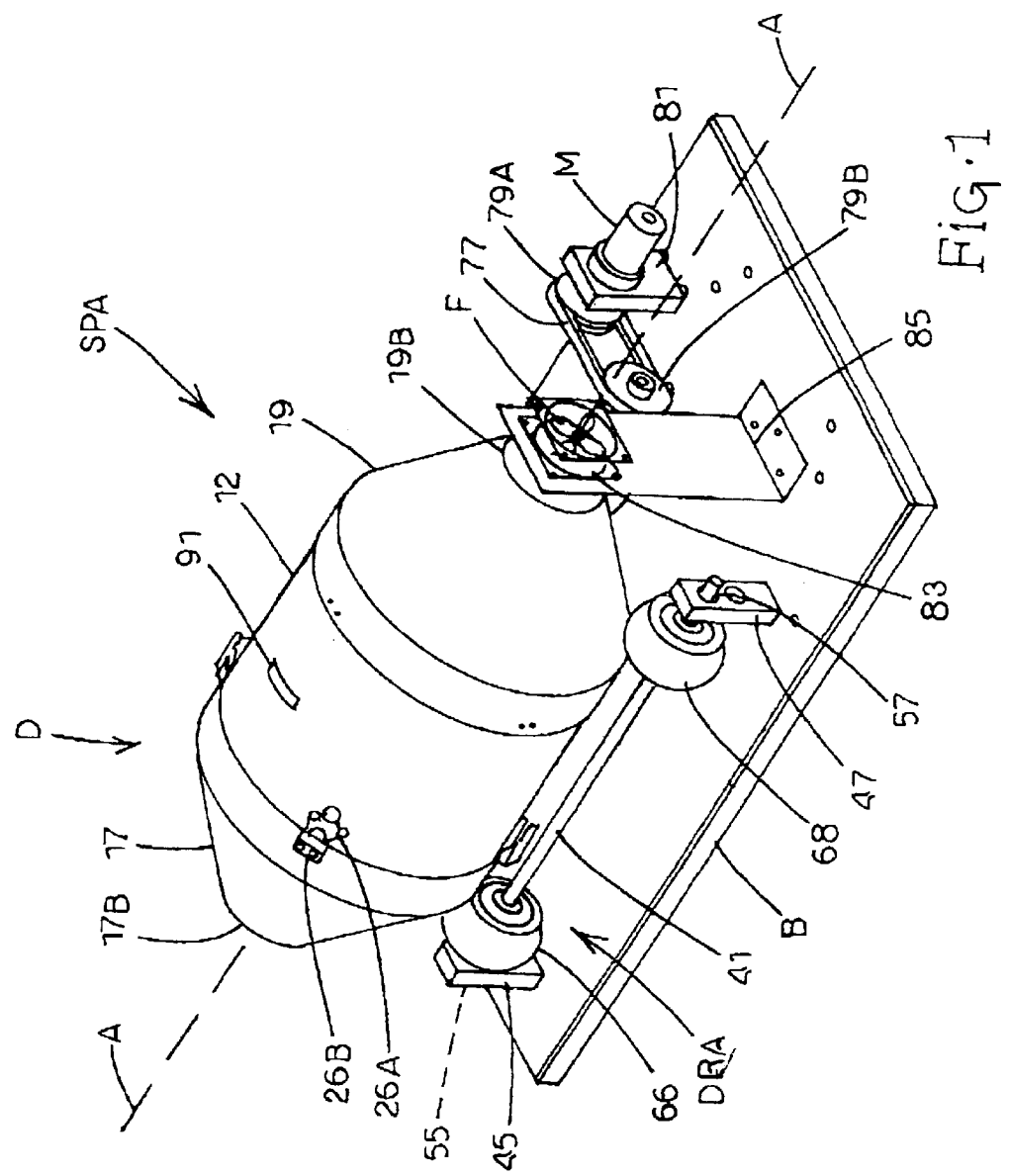
FIG. 1 is a perspective view of a sample preparation apparatus provided in accordance with the present invention.

Referring now to FIG. 1, a sample preparation apparatus, generally designated SPA, is illustrated. Sample preparation apparatus SPA comprises a rotatable container such as a drum, generally designated D; a drum rotation assembly, generally designated DRA; an air moving device such as a fan F; and a framework such as a base plate B suitable for supporting drum D and preferably also drum rotation assembly DRA and fan F. As described in more detail hereinbelow, drum D is adapted for containing, agitating (i.e., stirring or tumbling), and drying a mass of a material sample and, in particular, a solid sample or aggregate sample that is heatable. Non-limiting examples of material samples suitable for processing in drum include bituminous and/or aggregate materials such as asphalt, bituminous concrete, sand, and other fine mineral aggregates. Typically, such material samples contain internal and/or external voids capable of trapping or otherwise holding a liquid such as water. Drum rotation assembly DRA is adapted for supporting and rotating drum D about an axis of rotation A in an automated manner. Fan F is adapted for establishing a flow of fluid such as air through the interior enclosed by drum D so that a material sample contained in drum D is cooled and/or dried as desired.

Figure 2:
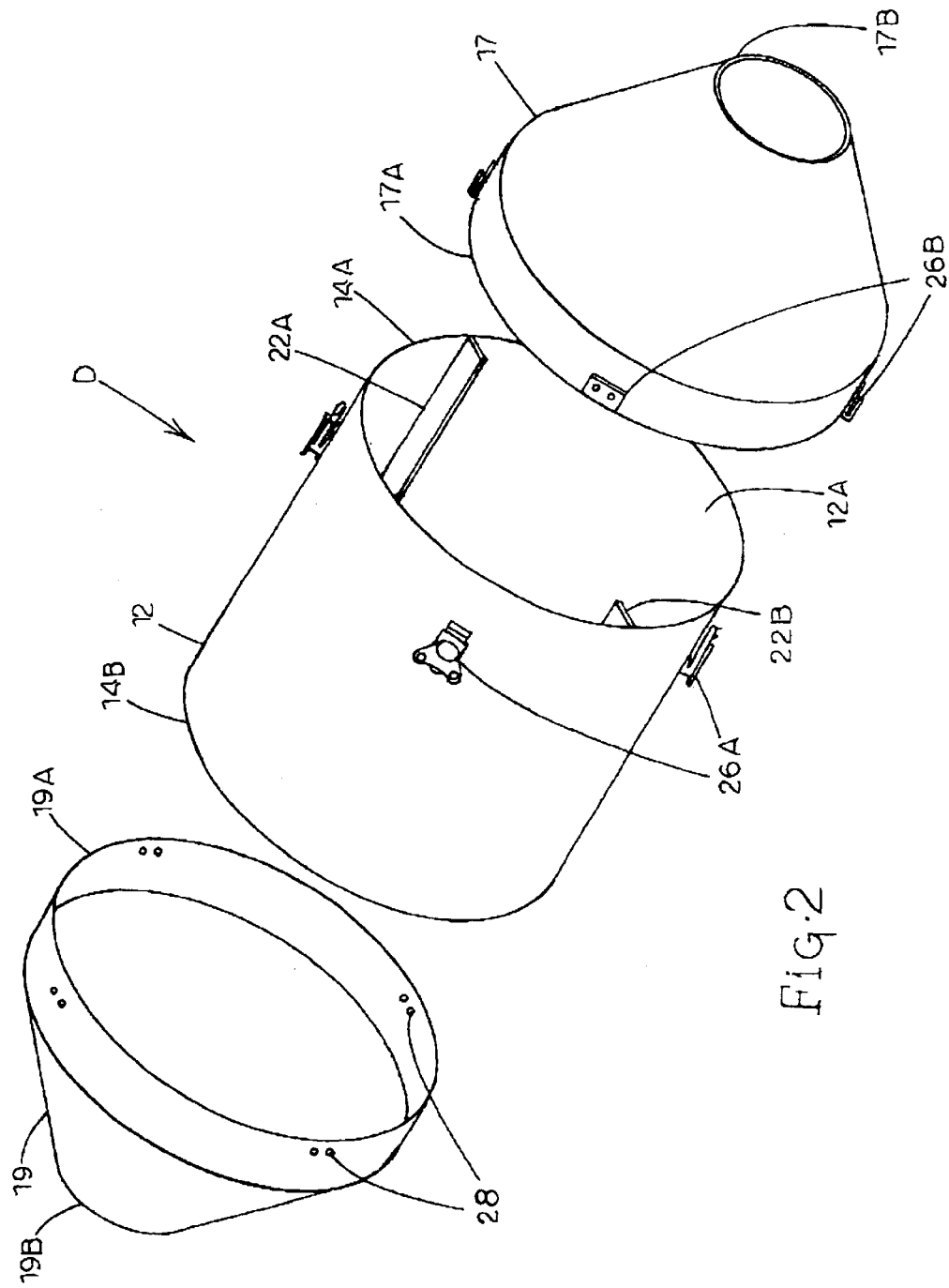
FIG. 2 is an exploded view of a drum provided with the sample preparation apparatus.

Referring to FIG. 2, drum D comprises a hollow main section 12 with first and second opposing open ends 14A and 14B, respectively, and first and second hollow end sections 17 and 19 serving as end caps for main section 12. To facilitate agitation and/or mixing of a material sample loaded into drum D while drum D is rotating, agitation elements 22A and 22B such as fins or baffles are mounted within main section 12 to interact with the material sample. Preferably, agitation elements 22A and 22B are mounted to an inside wall surface 12A of drum D and extend substantially radially inwardly toward axis of rotation A. Two agitation elements 22A and 22B mounted 180 degrees apart have been found sufficient in the practice of the invention as specifically illustrated in FIG. 2, though more may be used. Main section 12 is preferably cylindrical as illustrated, but could be rectilinear or otherwise polygonal.

The respective walls of first and second hollow end sections 17 and 19 of drum D taper from respective first and second inner apertures 17A and 19A to respective, smaller-diameter first and second outer apertures 17B and 19B. Preferably, first and second end sections 17 and 19 are frustoconical and main section 12 is cylindrical. In the case where main section 12 of drum D is not cylindrical, first and second end sections 17 and 19 could be predominantly pyramidal in shape, or could have any other shape characterized by a tapering profile. First inner aperture 17A of first end section 17 fits onto first open end 14A of main section 14, and second inner aperture 19A of second end section 19 fits onto second open end 14B of main section 14.

At least one of end sections 17 and 19 is removably attached to main section 12, although both first and second end sections 17 and 19 could be removably attachable. In the illustrated embodiment, first end section 17 is removably attached to main section 12 by providing a suitable quickly releasable fastener system, such as one or more interlocking buckle-type fastener components 26A and 26B mounted on the respective peripheries of first end section 17 and main section 12 at or near their corresponding open end regions. The ability to detach first end section 17 from main section 12 facilitates access into the interior of drum D for cleaning drum D. Second end section 19 is either removably or permanently attached to main section 12 by means of one or more fasteners 28 such as rivets, screws, or the like. First and second outer apertures 17B and 19B can each be provided with a screen 31, such as screen 31 shown in FIG. 5, but such screens are not needed for retaining a material sample within drum D as that function is accomplished by the tapered profile of first and second end sections 17 and 19.

In one specific, exemplary embodiment of drum D, the respective outside diameters of main section 12, first inner aperture of 17A first end section 17, and second inner aperture 19A of second end section 19 are each approximately 12 inches. The axial length of drum D from first outer aperture 17B to second outer aperture 19B is approximately 24 inches. The respective diameters of first and second outer apertures 17B and 19B are each approximately 4.2 inches. These dimensions enable the overall footprint of sample preparation apparatus SPA to be minimized and thus enable sample preparation apparatus SPA to be placed on a lab bench.

Figure 3:
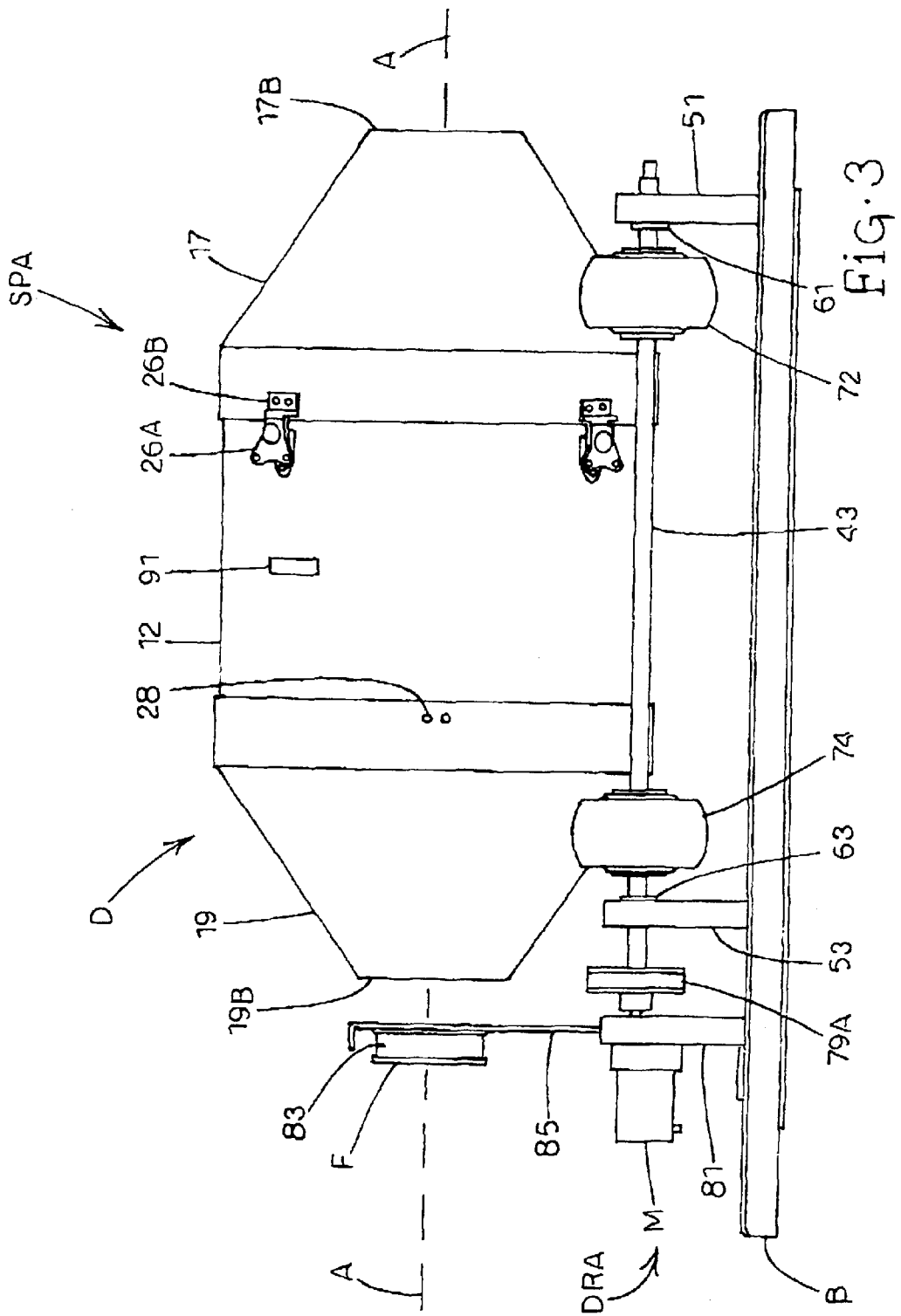
FIG. 3 is a side elevation view of the sample preparation apparatus.
Figure 4:
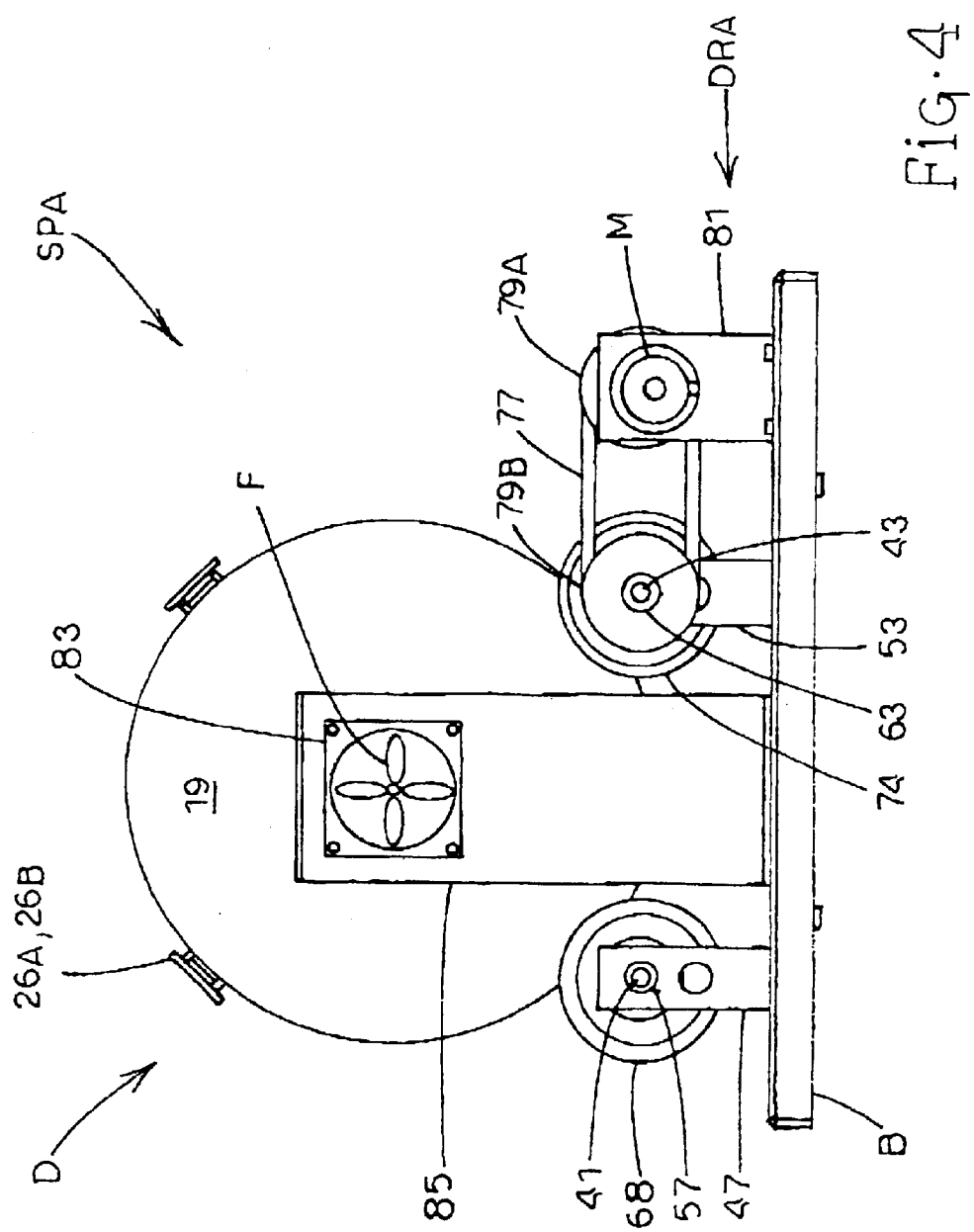
FIG. 4 is a front elevation view of the sample preparation apparatus.
Figure 5:
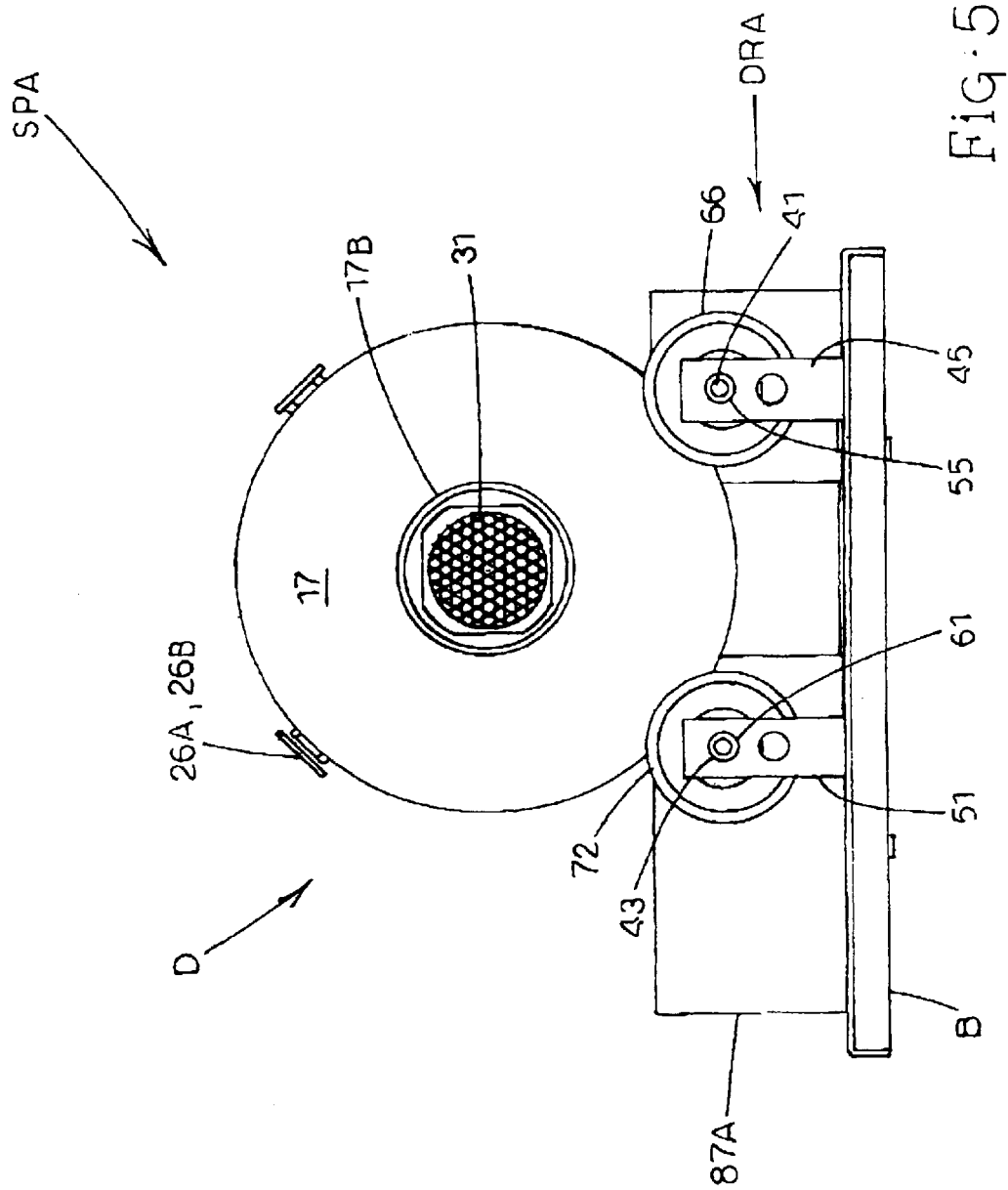
FIG. 5 is a rear elevation view of the sample preparation apparatus.

Referring back to FIG. 1 as well as FIGS. 3–5, drum rotation assembly DRA is suitable for supporting and driving drum D for rotation about axis of rotation A that preferably is oriented along or substantially along the horizontal. In the illustrated embodiment, drum rotation assembly DRA comprises first and second axles 41 and 43. As shown in FIG. 1, first axle 41 is rotatably mounted at its ends to a pair of first and second bearing blocks 45 and 47, which are in turn supported by base plate B. As shown in FIG. 3, second axle 43 likewise is rotatably mounted at its ends to a pair of third and fourth bearing blocks 51 and 53 supported by base plate B. Suitable sleeve bearings 55, 57, 61 and 63 such as bronze sleeve bearings are interposed between each bearing block 45, 47, 51 and 53 and corresponding axle 41 and 43. The respective pairs of bearing blocks 45, 47, 51, and 53 are situated on base plate B such that first and second axles 41 and 43 are oriented parallel or substantially parallel to base plate B and offset from axis of rotation A. In this manner, drum D is fully supported on first and second axles 41 and 43 so as to rotate about axis of rotation A in a stable and uniform manner. To improve the stability of drum D rotation and frictional contact between drum D and first and second axles 41 and 43, a pair of first and second rollers 66 and 68 are coaxially mounted to first axle 41 and a pair of third and fourth rollers 72 and 74 are coaxially mounted to second axle 43. Preferably, as shown in FIGS. 1 and 3, roller pairs 66, 68 and 72, 74 are located such that mechanical communication between drum D and first and second axles 41 and 43 actually occurs between first end section 17 and rollers 66 and 72, and between second end section 19 and rollers 68 and 74. As an example, each roller 66, 68, 72 and 74 can take the form of a 4-inch nominal-diameter rubber wheel.

With continuing reference to FIGS. 1 and 3–5, at least one of first and second axles 41 and 43 is driven by a source of rotational power so as to drive the rotation of drum D in an automated fashion. In the illustrated embodiment, second axle 43 is coupled to a power source in the form of a motor M. Motor M can be a conventional electric motor operative at 12 VDC, 24VDC, or 120 VAC. The rotating output shaft (not shown) of motor M can be directly coupled to second axle 43 or, as specifically illustrated, can be disposed offset from second axle 43 and coupled through a suitable transmission assembly such as a drive belt 77 wound around pulleys 79A and 79B. Motor M is mounted to a motor mounting bracket or block 81, which in turn is supported by base plate B.

Figure 6:
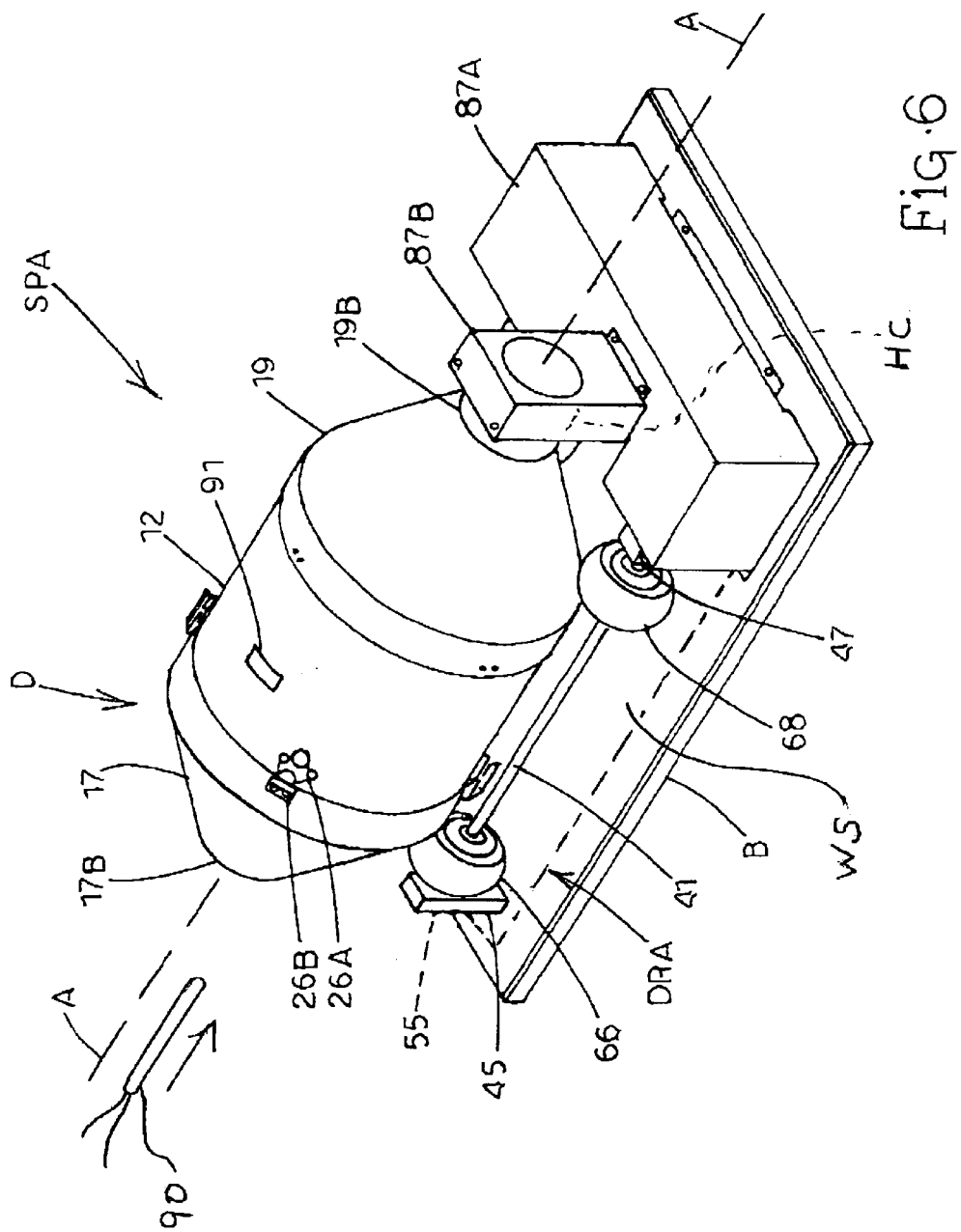
FIG. 6 is a perspective view of the sample preparation apparatus in which certain operative components are enclosed by cover members.

As indicated hereinabove, fan F is adapted for establishing a flow of fluid such as air through the interior enclosed by drum D. In the exemplary sample preparation methods described herein, the air moved by fan F is at a room or ambient temperature. However, as can be appreciated by persons skilled in the art, fan F could be incorporated into a closed fluid system in which cooled or heated air is circulated through drum D. Although in the illustrated example fan F is an axial-flow type unit in which the blades of fan F rotate about an axis coincident or substantially coincident with axis of rotation A, it can be appreciated that fan F could be a blower-type unit that includes a scroll-shaped or involute fan housing. Fan F can be configured to either blow or pull air through drum D. Referring to FIGS. 1 and 3, fan F preferably blows air through drum D, such that the direction of air flow is from second outer aperture 19B of second end section 19, through the interior of drum D, and out from first outer aperture 17B of first end section 17. Fan F can be a conventional unit operating at 12 VDC, 24VDC, or 120 VAC. Fan F is enclosed in a fan shroud 83 in a conventional manner. Fan F is elevated from base plate B so as to be aligned or substantially aligned with second outer aperture 19B by mounting fan F or its shroud 83 to a fan mounting bracket 85, which is in turn supported by base plate B. Base plate B can be constructed from any material suitable for supporting drum D, drum rotation assembly DRA, and fan F, with one example being aluminum. As shown in FIG. 6, cover members 87A and 87B can be provided to enclose motor M, fan F, and associated components and wiring. In addition, a heating coil HC or other suitable heating element could be mounted within lower member 87B to heat the air supplied by fan F if desired.

In operation, sample preparation apparatus SPA can be used to as part of any sample preparation process that requires mixing, tumbling and/or drying, and which could benefit from the savings in time and labor associated with automating such mixing, tumbling and drying procedures. Accordingly, referring generally to FIGS. 1–6, the invention provides a general method of sample preparation involving the following steps. Sample preparation apparatus SPA is provided preferably in accordance with the embodiment described above and illustrated in FIGS. 1–6. First end section 17 is detached from main section 12 of drum D, a material sample is loaded into drum D, and first end section 17 is then re-attached to main section 12. Motor M is then activated to initiate rotation of drum D, thereby agitating the mass of sample loaded therein. Fan F is activated to establish air flow through drum D. Depending on the initial temperature of the sample relative to that of the air flowing through drum D, the air flow causes heat energy to be transferred either to or from the sample. While drum D is rotating and air is flowing through drum D, a property of the sample such as temperature or mass can be monitored. The monitoring of temperature can be done directly by inserting a suitable temperature probe such as a thermocouple 90 (FIG. 6) into or onto the sample, or by providing one or more readily available temperature strips 91 on the outer wall surface of drum D as shown in FIGS. 1, 3 and 6. While temperature strip 91 indicates the temperature of the wall of drum D, this can be correlated to the temperature of the sample. Alternatively, if the tumbling and/or drying process is allowed to continue for a sufficient period of time, the temperature indicated by temperature strip 91 can be assumed to correspond to the temperature of the sample. Once a target temperature has been reached, fan F and motor M are de-activated, first end section 17 detached from main section 12 of drum D, and the prepared sample then removed from drum D.

In the practice of any sample preparation method of the invention, the tapering profile of first and second end sections 17 and 19 of drum D is an advantageous feature. As drum D is rotated about axis of rotation A, the mass of sample loaded in drum D tends to spread out toward first and second outer apertures 17B and 19B. The spreading sample will encounter the inclined inside walls of the tapered regions of first and second end sections 17 and 19 and be rolled back to a centered position along main section 12. In this manner, the sample is prevented from being discharged from drum D through first and second outer apertures 17B and 19B.

In one specific method of the invention, a bituminous paving material sample such as a mass of asphalt is processed by sample preparation apparatus SPA to produce a loose, cool sample in preparation for a laboratory test such as the above-described ASTM D2041 test (Rice test) or other test for specific gravity or density. The mass (for example, up to 6000 g) of asphalt or other appropriate material sample is heated to 100+/−5° C. in a suitable oven. In accordance with the general method described above, the heated sample is then loaded into drum D and rotation of drum D is initiated by activating motor M. In one embodiment, drum D rotates at 40+/−5 rpm. Air flow through drum D is then established by activating fan F. Preferably, drum D is rotated for approximately one minute prior to activating fan F. The operation of fan F is delayed in this manner because, in many cases, contact of the sample with the initially cold drum D will result in rapid conductive cooling during this initial phase of the procedure. Moreover, too much cooling during the initial phase could lead to undesirable clumping of the sample. The temperature of drum D is monitored as also described above. The target temperature is 25° C. or ambient room temperature, whichever is greater. When the target temperature is reached, preparation of the sample is complete and the sample can be removed for subsequent testing such as the Rice test, in which the specific gravity of the cooled, loose sample is determined. Sample preparation apparatus SPA provided in accordance with at least one embodiment of the invention is capable of cooling up to 6000 g of bituminous material without a material loss of more than 0.015%.

In another specific method of the invention, a wet sample aggregate material such as sand, gravel, stone or other mineral is processed by sample preparation apparatus SPA to bring the aggregate sample to its SSD state in preparation for further testing, such as the above-described aggregate tests for determining specific gravity and absorption. The aggregate sample is initially wetted such as by immersion in water for twenty-four hours. In accordance with the general method described above, the wet sample is then loaded into drum D and rotation of drum D is initiated by activating motor M. In one embodiment, drum D rotates at 40+/−5 rpm as previously described. Once drum D has rotated for about one minute, air flow through drum D is established by activating fan F. At appropriate intervals (for example, every fifteen minutes), drum D and the sample contained therein are weighed. The weighing can be accomplished by removing drum D from sample preparation apparatus SPA and placing drum D on a suitable scale. Alternatively, a weight scale WS could be integrated with base plate B or other supporting component of sample preparation apparatus SPA, as schematically shown in FIG. 6. In either case, the weight of all non-sample components is subtracted from the weight readings in order to determine the weight of the sample. The steps of rotating drum D, operating fan F, and weighing the sample are repeated until the loss of sample mass per time interval is less than a specific level (0.05% for a 15 minute interval), at which point the sample is considered to be at the SSD state. As an alternative to weighing the sample, the humidity of the air exhausting from drum D (i.e., the output from first outer aperture 17B of first end section 17) can be monitored by conventional means, in which case the SSD condition could be defined at the occurrence of an inflection point in a recorded humidity vs. time plot.

As compared to the conventional testing methods described hereinabove, the methods of the present invention can result in significant time savings.

It is therefore seen from the foregoing that an apparatus and method are provided for preparing material samples such as paving materials in an automated manner so as to render such samples suitable for commonly performed tests in which properties such as specific gravity, density, and/or absorption are determined.

It will be understood that various details of the invention may be changed without departing from the scope of the invention. Furthermore, the foregoing description is for the purpose of illustration only, and not for the purpose of limitation, as the invention is defined by the claims as set forth hereinafter.

What is claimed is:

1. A method for preparing a material sample, comprising the steps of:
    (a) placing a material sample in a drum, the drum comprising a hollow main section having first and second open ends, a hollow first tapered section attached to the first open end and tapering to a first outer aperture, and a hollow second tapered section attached to the second open end and tapering to a second outer aperture, wherein the drum is rotatably supported on a support assembly;
    (b) rotating the drum with a motor;
    (c) conducting a flow of air through the drum whereby heat transfer occurs between the air and the sample;
    (d) monitoring a property of the sample; and
    (e) when the property reaches a desired value, de-activating the motor to cease rotation of the drum.

2. The method according to claim 1 wherein the sample is selected from the group consisting of bituminous materials, minerals, aggregate materials, and combinations thereof.

3. The method according to claim 1 comprising heating the sample prior to placing the sample in the drum, wherein conducting the flow of air through the drum causes the sample to be cooled.

4. The method according to claim 1 wherein rotating the drum comprises operating a motor to rotatably drive the drum support assembly.

5. The method according to claim 1 comprising removing the sample from the drum after the sample property has reached the desired value, and determining a value for specific gravity of the sample.

6. The method according to claim 1 comprising removing the sample from the drum after the sample property has reached the desired value, and determining a value for absorption of the sample.

7. A method for preparing a material sample, comprising the steps of:
   (a) placing a heated material sample in a drum, the drum comprising a hollow main section having first and second open ends, a hollow first tapered section attached to the first open end and tapering to a first outer aperture, and a hollow second tapered section attached to the second open end and tapering to a second outer aperture, wherein the drum is rotatably supported on a support assembly;
   (b) activating a motor connected to the support assembly to rotate the drum;
   (c) cooling the sample by activating a fan to establish forced air flow through the drum;
   (d) monitoring a temperature of the sample; and
   (e) when the sample temperature reaches a desired sample temperature, de-activating the motor to cease rotation of the drum.

8. The method according to claim 7 wherein monitoring the sample temperature comprises monitoring a temperature of the drum, and rotation of the drum is ceased when the drum temperature reaches a desired drum temperature equal to or at least approximating the desired sample temperature.

9. The method according to claim 8 wherein monitoring the drum temperature comprises monitoring a temperature strip attached to the drum.

10. The method according to claim 8 wherein the desired drum temperature is the greater of approximately 25° C. or ambient temperature.

11. The method according to claim 7 comprising removing the sample from the drum after the sample property has reached the desired sample temperature, and determining a value for specific gravity of the sample.

* * * * *